United States Patent [19]
McGee et al.

[11] Patent Number: 5,811,755
[45] Date of Patent: Sep. 22, 1998

[54] WELD REPAIR METHOD FOR ALUMINUM LITHIUM SEAM

[75] Inventors: William Floyd McGee, Slidell, La.; Daniel John Rybicki, Huntsville, Ala.

[73] Assignee: Lockheed Martin Corp., New Orleans, La.

[21] Appl. No.: 584,901

[22] Filed: Jan. 11, 1996

[51] Int. Cl.⁶ .................................................... B23K 9/00
[52] U.S. Cl. ......................... 219/137 WM; 219/124.21; 228/119
[58] Field of Search .................. 219/137 WM, 219/124.21, 125.1, 128, 137 R; 228/119; 29/402.01, 402.02, 402.09, 402.11

[56] References Cited

U.S. PATENT DOCUMENTS

| | | |
|---|---|---|
| 3,192,618 | 7/1965 | Altgelt .................................. 228/119 |
| 4,049,186 | 9/1977 | Hanneman et al. . |
| 4,285,459 | 8/1981 | Baladjanian et al. . |
| 4,458,125 | 7/1984 | Leis . |
| 4,493,451 | 1/1985 | Clark et al. . |
| 4,575,611 | 3/1986 | Bertossa . |
| 4,624,402 | 11/1986 | Pitcairn et al. . |
| 4,959,523 | 9/1990 | Fihey et al. ......................... 219/125.1 |
| 5,071,054 | 12/1991 | Dzugan et al. ........................ 228/119 |
| 5,156,321 | 10/1992 | Liburdi et al. . |
| 5,258,600 | 11/1993 | Arthur . |

*Primary Examiner*—Clifford C. Shaw
*Attorney, Agent, or Firm*—W. H. Meise; S. A. Young

[57] ABSTRACT

Aluminum-lithium plates are butt-welded by juxtaposing the plates and making a preliminary weld from the rear or root side of the seam. An initial weld is then made from the face side of the seam, which may cause a defect in the root portion. A full-size X-ray is made and overlain over the seam to identify the defects. The defect is removed from the root side, and rewelded. Material is then removed from the face side, and the cavity is rewelded. The procedure repeats, alternating from the root side to the face side, until the weld is sound.

10 Claims, 4 Drawing Sheets

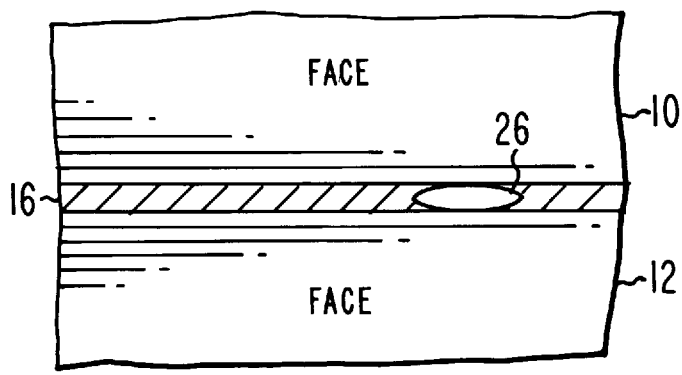
Fig. 1i
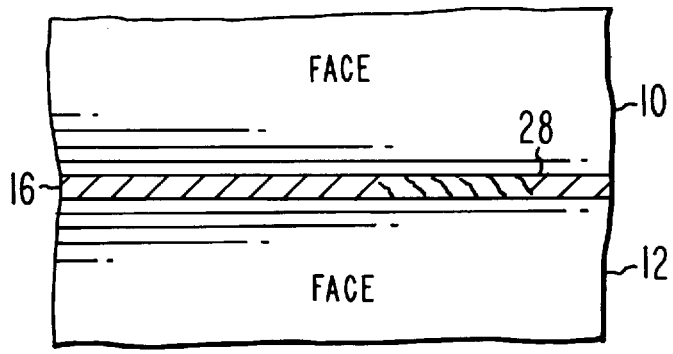
Fig. 1j
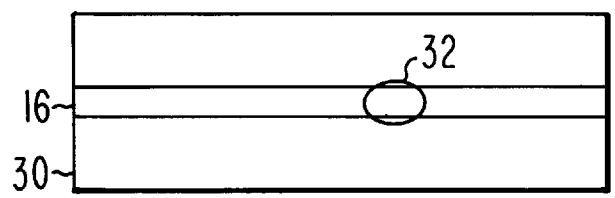
Fig. 1k
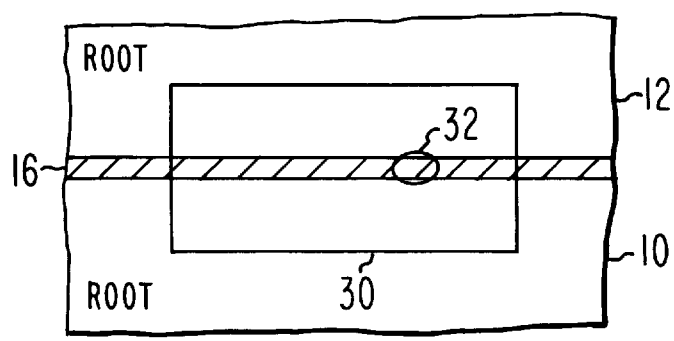
Fig. 1ℓ

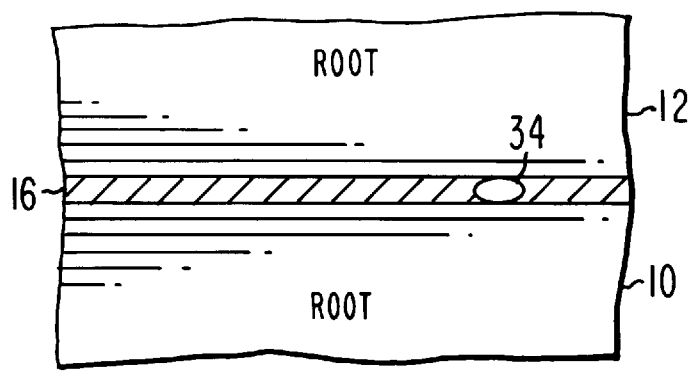
Fig.1m
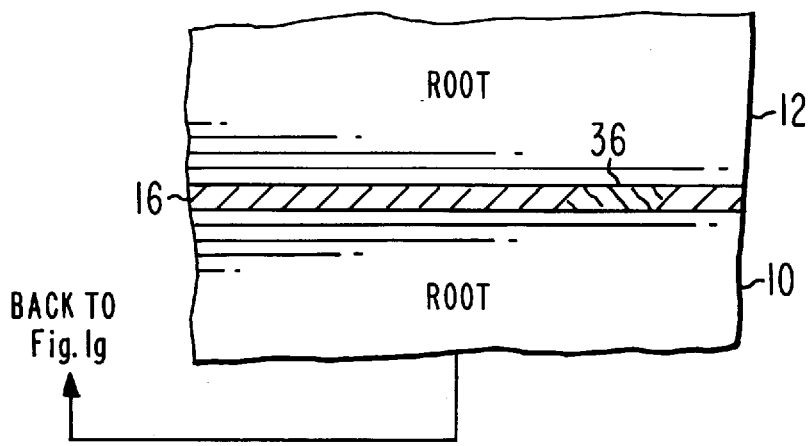
Fig.1n
BACK TO
Fig.1g

WELD REPAIR METHOD FOR ALUMINUM LITHIUM SEAM

This invention was made under NASA contract NAS 8-36200, on which waiver number W-3047 has been granted.

FIELD OF THE INVENTION

This invention relates arrangements and methods for correcting or repair of defects in aluminum-lithium seams, especially for those of a lightweight propellant tank.

BACKGROUND OF THE INVENTION

The fuel tank for the space shuttle is made from a number of aluminum cylinders and two end domes, all welded together along seams to form a closed vessel for the storage of propellant, including liquid hydrogen. The internal pressure of the liquefied propellant, and the aerodynamic loads on the fuel tank during launch of the space shuttle, require extremely light weight and strong welds. Lithium-aluminum 2195 alloy has been proposed as a substitute for the aluminum currently being used for the fuel tank, because of its high strength and relatively light weight.

Unfortunately, it has been found that the welding of lithium-aluminum alloy is more difficult than the welding of aluminum alone, and defects tend to form in the weld region. The lithium-aluminum alloy forms a fusion line at the location of the weld due to the temperature reached by the metal adjacent the weld due to the welding heat. The fusion line has a microstructure which consists of fine equiaxed grains coated with solute element second phases.

It has been determined that the microstructure of the fusion line is detrimental to the integrity of the weld. However, repairs require re-welding. Too much heat input, including cumulative heat input from multiple and successive heating cycles, accompanied by the build-up of residual stresses induced by weld solidification shrinkage, tends to result in cracking at the fusion line. Thus, attempts to re-weld defective regions of the initial weld often extends the region over which the defect occurs.

SUMMARY OF THE INVENTION

A method according to the invention for welding an aluminum-lithium seam includes the preliminary step of juxtaposing first and second plate-like aluminum-lithium objects to be welded along their edges, and holding them in position. When so held, the juxtaposed objects or plates define face and reverse principal sides. An initial weld is made from the face side of the juxtaposed objects, by applying heat to a location along the seam to fuse and join the first and second objects at the heated location on the seam. The heated location is moved to fuse the length of the seam, as a result of which a region of defective weld may occur in a root side of the seam adjacent the reverse side of the objects. When such a defect is identified, the root portion of the defective weld is removed in the defective region, which leaves an unwelded root portion. Heat is applied from the reverse side of the objects, to a location along the unwelded root portion of the seam, to thereby fuse and join the first and second objects at the heated location on the seam. The heated location is moved to fuse and join the length of the unwelded root portion. The face portion of the defective weld is removed, which leaves an unwelded face portion. From the face side of the objects, heat is applied to a location along the unwelded face portion of the seam to fuse and join the first and second objects at the heated location, and the heated location is moved to fuse and join the length of the unwelded root portion. The steps of removing the root portion of the defective weld, applying heat to a location along the unwelded root portion of the seam and moving the location, removing the face portion of the defective weld, and applying heat to a location along the unwelded face portion of the seam and moving the location, are repeated in the specified order until no defective portion of the weld remains. the initial weld may be preceded by a preliminary weld to form the root portion of the weld. The step of removing includes the step of applying a toothed cutting or abrasive tool, which may be a rotating tool, to the weld in the defective portion for removing metal. The heat may be applied with an electrical torch, and inert gas may be applied to the heated region to reduce defects.

In a particular method according to the invention, a radiographic (X-ray) overlay is used to identify the region to be cut away.

BRIEF DESCRIPTION OF THE DRAWINGS

FIG. 1i represents cutting away material from the face side of the repaired weld of FIG. 1f in the region identified as being defective in FIG. 1h, FIG. 1j represents welding on the face side of the region in which material was removed in the step of FIG. 1i, FIG. 1k represents a radiographic image of the repair of FIG. 1i, FIG. 1l represents the overlaying of the radiographic image of FIG. 1k on the welded region, FIG. 1m represents removal of material from the root side of the weld in the region identified as defective by the image of FIG. 1k, and FIG. 1n represents the result of welding the region in which material was removed in the step of FIG. 1m.

DESCRIPTION OF THE INVENTION

It has been determined that a part of the original fusion microstructure a weld may be consumed, and a new fusion boundary or fusion line may form, when a second generation of weld is formed with lower heat input than the original weld.

Figure 1A:
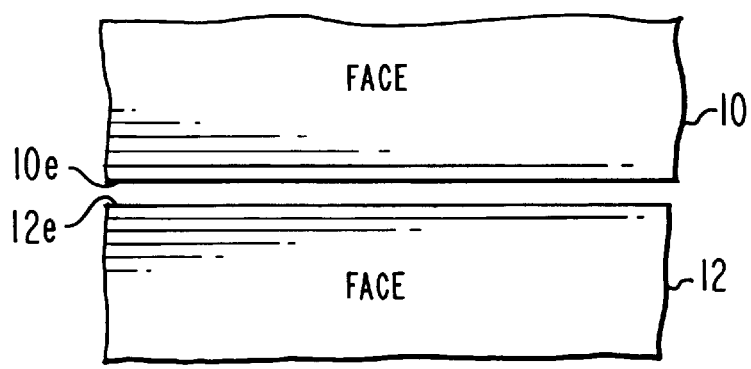
FIG. 1a illustrates the juxtaposition of two aluminum-lithium plates to be welded.
Figure 1B:
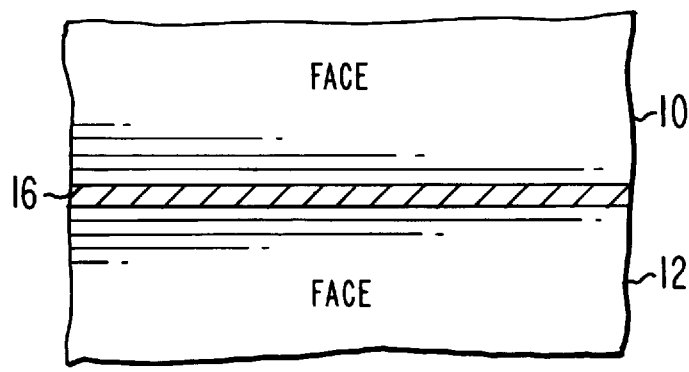
FIG. 1b represents application of a preliminary weld from the face side of the plates, to define a crown portion and a root region of a welded seam.

FIG. 1a illustrates a portion 10 of a lithium-aluminum alloy cylinder or dome, which is to be joined to a corresponding portion 12 of a second lithium-aluminum cylinder or dome along juxtaposed edges 10e and 12e. The cylinders or domes are sufficiently large so that, in the region depicted, they may be considered to be essentially flat plates. The illustrated portions of plates 10 and 12 are the side from which the weld is initially made, which may be considered to be the "outside" of the tank, and the illustrated portions of the plates are designated as being the "face" side. FIG. 1b represents the face sides of plates 10 and 12 after an initial weld 16 made from the face side of the plates, by applying heat at a location along the future seam, and moving the location of the application of heat along the seam to fuse the material.

Figure 1C:
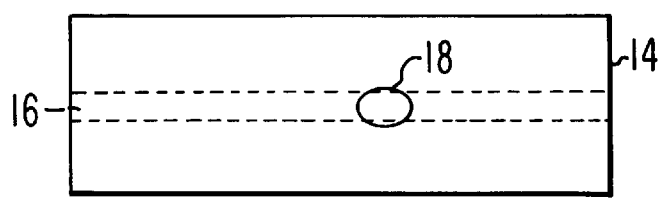
FIG. 1c represents the result of a radiographic image of the weld of FIG. 1b.

The weld can be examined by several methods. A preferred method for examination is to make radiographic images of the weld region, which exposes the defective portions of the weld. FIG. 1c represents a radiographic image of a portion of weld 16, illustrating a defective region designated 18. According to an aspect of the invention, the radiographic image is used to locate the site of the defect. This can be accomplished by making a full-size image of a selected region of the welded plates, and superposing the image on the welded plates to thereby identify the location of the defect. The tank is wrapped with a steel measuring tape having lead-impregnated markings during the exposure to the X-rays. The lead markings show up in the radiographic image, and allow the image to be registered with the tank to identify the location of defects.

The full-size image may be made by starting with a full-size negative, or a smaller negative may have its image projected at full size onto the welded region. The initial weld 16 made from the face side of the plates as described in conjunction with FIG. 1b defines a "crown" adjacent the face side of the plates and a "root" on the reverse side from the face side. The root side may be considered to correspond the "inside" of the tank. The inside of the tank is always accessible, even after fabrication, by way of access ports.

Figure 1D:
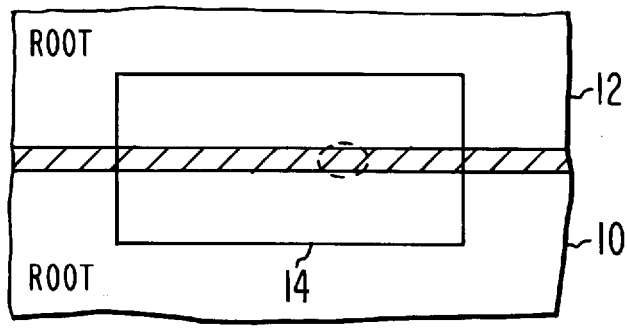
FIG. 1d represents overlaying the image of FIG. 1c on the weld of FIG. 1b.
Figure 1E:
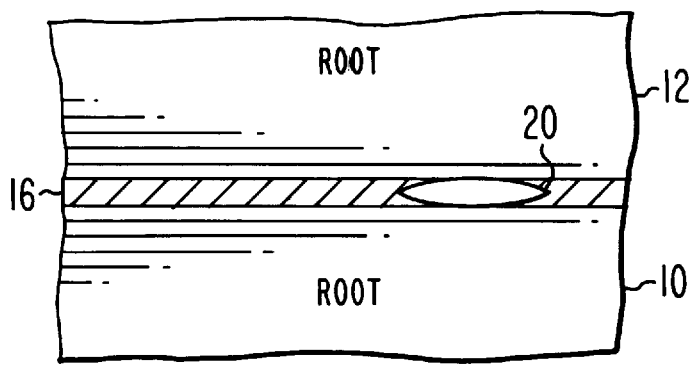
FIG. 1e represents the removal of material from the root side of the weld in the defective region.
Figure 1F:
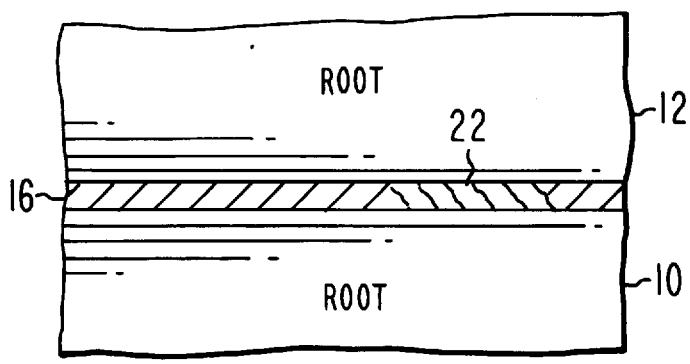
FIG. 1f represents welding repair of the material removed in the step of FIG. 1e.

According to another aspect of the invention, the first repair is made from the root side of the weld. Once the location of the defect is identified by examination, as suggested by FIG. 1c, and by identifying the location of the defect, as by overlaying the weld with a radiographic image as described in conjunction with FIG. 1d, the defective portion of the welded region is mechanically removed in the defect region. If the defect is visible only in the radiographic image, the material is removed only half-way through the thickness of the weld. It often happens that, as material is removed, the defect becomes visible to the naked eye, in which case sufficient material is removed to excise at least the visible portion. The mechanical removal is preferably performed by a suitable tool, such as an electrically or pneumatically driven rotary toothed cutter or abrasive disk. The result of the removal of the defective portion of the weld is illustrated in FIG. 1e, where the portion removed is designated 20. The next step is to again apply heat, in order to fuse region 20. Since material was removed, it may be necessary to supply additional material to aid in filling the void; no suitable lithium-aluminum wire is known, and the filling is accomplished with 4043 aluminum material. The result of the first repair weld is illustrated in FIG. 1f, where repaired region 20 is designated as 22.

Figure 1G:
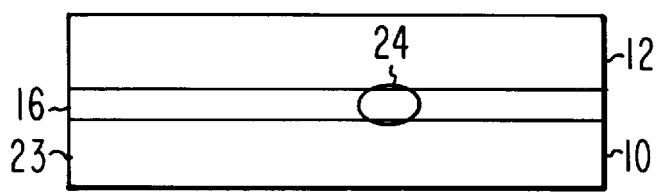
FIG. 1g represents a radiographic image of the repaired weld of FIG. 1f.
Figure 1H:
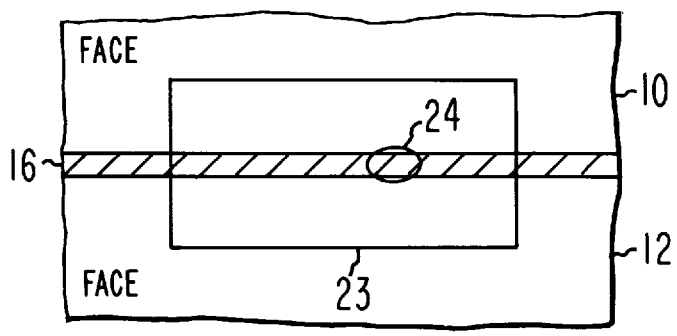
FIG. 1h represents overlaying the radiographic image of FIG. 1g on the repaired weld of FIG. 1f.

After the first repair from the root side, the weld is again examined. Ideally, the repaired weld will be sound, and no further repair will be required. Often, however, the weld will contain new fusion lines representing defects arising from the heat applied during the initial and first repair welds. The result of a radiographic examination which reveals a further defect is illustrated in FIG. 1g, where a defective region 24, smaller than original defective region 18, is illustrated. FIG. 1h illustrates application of radiographic image 23 to the weld to identify the location of the new defect. According to the invention, the material in defective region 24 is removed from the original crown of the weld on face side of the plates being welded, as illustrated by region 26 in FIG. 1i. The weld is repaired by further application of heat to region 26 as illustrated in FIG. 1j, where the filled-in region is designated 28.

After the welding step illustrated in FIG. 1j, the weld is again examined. Naturally, if no defect is identified, the procedure stops. If, however, a further defect is identified, as suggested by region 32 of the radiographic image 30 of FIG. 1k, the material is removed from the root side in the region of the defective weld, as suggested by the overlay step of FIG. 1l and the removal step of FIG. 1m. In FIG. 1m, the defective region 34 is likely to be smaller than the previous defective regions. FIG. 1n represents the result of fusing the region 34, to produce a repaired welded region designated 36.

After the step represented by FIG. 1n, the next step is to again examine the weld, and stop the repair process if appropriate. In effect, the repair process repeats steps 1g, 1h, 1i, 1j, 1k, 1l, 1m, and 1m until the defect is cured.

Thus, making a defect-free lithium-aluminum weld according to the invention involves starting the weld from a face side, examining the weld, and if it is defective, removing material from the reverse side of the weld (the root side in the case of repair of the initial weld). The material is welded in the removed region, and again examined. If defects are found, material is removed from the reverse side of the last repair performed, and again welded. This alternation is repeated until the weld is defect-free.

Other embodiments of the invention will be apparent to those skilled in the art. For example, while the removal of material from the defective region has been described as being performed with rotary power tools, other metal removal methods, such as hand tools or lasers, may be used. While radiographic images have been described, acoustic or other images may be used, or the defect may be located by various methods by the worker who performs the repair. If a suitable lithium-aluminum wire is found which can be used as a filler material, it may be used instead of the aluminum filler wire. The filler wire may be used in forming the initial weld, if necessary. While large tanks of lithium-aluminum material are the particular subjects of the welding method, it may be applied to any welds of lithium-aluminum material which, when initially welded, defines a crown and a root, and is, in principle, not limited to straight seams.

What is claimed is:

1. A method for welding a seam in a material which tends to generate defects arising from the application of fusion heat, comprising the steps of:

juxtaposing first and second plate-like objects of said material to be welded along a butt seam therebetween, said juxtaposing being such as to define face and reverse principal sides of said juxtaposed objects;

making an initial weld from said face side of said juxtaposed objects by applying heat to a location along said seam to fuse said first and second objects at said location on said seam, and moving said location to fuse the length of said seam, as a result of which a region of defective weld may occur in a root side of said seam adjacent said reverse side of said objects;

removing the root portion of said defective weld in said region, which leaves an unwelded root portion;

from said reverse side of said objects, applying heat to a location along said unwelded root portion of said seam to fuse and join said first and second objects at said location on said seam, and moving said location to fuse and join the length of said unwelded root portion;

removing the face portion of said defective weld in said region, which leaves an unwelded face portion;

from said face side of said objects, applying heat to a location along said unwelded face portion of said seam to fuse and join said first and second objects at said location, and moving said location to fuse and join the length of said unwelded root portion; and repeating said steps of removing the root portion of said defective weld, applying heat to a location along said unwelded root portion of said seam and moving said location, removing the face portion of said defective weld, and applying heat to a location along said unwelded face portion of said seam and moving said location, until the defective portion of said weld is removed.

2. A method according to claim 1, wherein said step of removing includes the step of applying a cutting tool to said weld in said defective portion for removing metal.

3. A method according to claim 2, wherein said step of applying a cutting tool comprises the step of applying a rotating toothed cutter.

4. A method according to claim 2, wherein said step of applying a cutting tool comprises the step of applying a rotating abrasive cutter.

5. A method according to claim 1, wherein said step of applying heat includes the step of applying plasma from an electrical torch to said seam.

6. A method according to claim 5, further comprising the step of applying an inert gas to said seam during said step of applying heat.

7. A method according to claim 1, further comprising the step of:

prior to said making said initial weld, making a preliminary weld along said seam from said reverse side of said juxtaposed first and second objects, to thereby form said root side of said seam.

8. A method according to claim 1, wherein said material is lithium-aluminum alloy.

9. A method according to claim 1, further comprising the step of examining said seam with penetrating radiation before said steps of removing, to thereby reveal said defective portions, and making a full-size record of at least said defective portions; and after said step of examining, and before said steps of removing, placing said record over said seam to thereby identify the location at which removing should be performed.

10. A method according to claim 9, further comprising the step of applying measurement indicia to said weld before said step of examining said seam with penetrating radiation, for forming images of said measurement indicia on said radiographic record.

* * * * *